(12) United States Patent
Malfliet et al.

(10) Patent No.: US 8,706,672 B2
(45) Date of Patent: Apr. 22, 2014

(54) COMPUTER-ASSISTED CREATION OF A CUSTOM TOOTH SET-UP USING FACIAL ANALYSIS

(75) Inventors: Katja Malfliet, Bierbeek (BE); Veerle Pattijn, Kersbeek-Miskom (BE); Carl Van Lierde, Meerbeke (BE); Wilfried Vancraen, Huldenberg (BE)

(73) Assignee: Dentsply Implants NV, Hasselt (BE)

( * ) Notice: Subject to any disclaimer, the term of this patent is extended or adjusted under 35 U.S.C. 154(b) by 523 days.

(21) Appl. No.: 12/596,231

(22) PCT Filed: Apr. 10, 2008

(86) PCT No.: PCT/EP2008/003072
§ 371 (c)(1),
(2), (4) Date: Oct. 16, 2009

(87) PCT Pub. No.: WO2008/128700
PCT Pub. Date: Oct. 30, 2008

(65) Prior Publication Data
US 2010/0145898 A1 Jun. 10, 2010

(30) Foreign Application Priority Data
Apr. 18, 2007 (GB) .................................. 0707454.5

(51) Int. Cl.
| G06F 17/00 | (2006.01) |
| G06N 5/02 | (2006.01) |
| G06G 7/48 | (2006.01) |
| A61C 3/00 | (2006.01) |
| G06F 19/00 | (2011.01) |
| A61C 13/00 | (2006.01) |

(52) U.S. Cl.
USPC .................. 706/47; 703/11; 433/24; 700/97; 700/98; 264/16

(58) Field of Classification Search
None
See application file for complete search history.

(56) References Cited

U.S. PATENT DOCUMENTS 7,234,937 B2 * 6/2007 Sachdeva et al. ............... 433/24
7,970,628 B2 * 6/2011 Kuo et al. ......................... 705/2

(Continued)

FOREIGN PATENT DOCUMENTS

| JP | 2005168518 A | 6/2005 |
| WO | 2004098378 A2 | 11/2004 |

(Continued)

OTHER PUBLICATIONS

Motohashi, N and Kuroda, T. "A 3D computer-aided design system applied to diagnosis and treatment planning in orthodontics and orthognathic surgery." The European Journal of Orthodontics. 21.3 (1999): 263-274.*

(Continued)

*Primary Examiner* — Kakali Chaki
*Assistant Examiner* — Daniel Pellett
(74) *Attorney, Agent, or Firm* — Bacon & Thomas, PLLC (57) ABSTRACT

A method for automatic, or semi-automatic, planning of dental treatment for a patient comprises: (a) obtaining data about an area which is to be treated and data about a face of a patient; (b) performing a computer-assisted analysis of the data to determine properties of at least the face of the patient; (c) creating a modified tooth set-up using a set of stored rules which make use of the determined facial properties. A three-dimensional representation simulates the appearance of the modified tooth set-up and the patient's face surrounding the treatment area. The method also determines properties of existing teeth and creates a modified tooth set-up which is also based on the existing teeth of the patient. The method can be implemented as software running on a workstation.

19 Claims, 7 Drawing Sheets

(56) References Cited

U.S. PATENT DOCUMENTS

| | | |
|---|---|---|
| 8,126,726 B2* | 2/2012 | Matov et al. ............... 705/2 |
| 8,170,327 B2* | 5/2012 | Glor et al. ............... 382/154 |
| 2005/0038669 A1* | 2/2005 | Sachdeva et al. ............... 705/2 |
| 2009/0187393 A1* | 7/2009 | Van Lierde et al. ............ 703/11 |

FOREIGN PATENT DOCUMENTS

| | | |
|---|---|---|
| WO | 2004098379 A2 | 11/2004 |
| WO | 2006000063 A1 | 1/2006 |

OTHER PUBLICATIONS

PCT International Publication No. WO 2006/000063 A1.*
Ishibuchi, H.; Yamamoto, T.; , "Rule Weight Specification in Fuzzy Rule-Based Classification Systems," Fuzzy Systems, IEEE Transactions on , vol. 13, No. 4, pp. 428- 435, Aug. 2005.*
Glor et al., PCT Publication WO 2007/009719.*
Besl, P.J and McKay, N.D., "A Method for Registration of 3-D Shapes" IEEE Transactions on Pattern Analysis and Machine Intelligence, vol. 14, No. 2, pp. 239-256, Feb. 1992.
Estepar et al., "Robust Generalized Total Least Squares Iterative Closest Point Registration", C. Barillot, D.R. Haynor, and P. Heltier (Eds.): MICCAI 2004, LNCS 3216, pp. 234-241, 2004.
Gruen, A. and Akca, D., "Least squares 3D surface and curve matching", ISPRS Journal of Photogrammetry & Remote Sensing 59(3), pp. 151-174, May 2005.
International Search Report in PCT/EP2008/003072, Aug. 11, 2008.
Japanese Office Action for JP 2010-503408 dated Oct. 30, 2012, and English translation thereof.
Japanese Office Action for corresponding JP 2010-503408, dated Aug. 20, 2013, and English translation thereof.

* cited by examiner

COMPUTER-ASSISTED CREATION OF A CUSTOM TOOTH SET-UP USING FACIAL ANALYSIS

FIELD OF THE INVENTION

This invention relates generally to the field of computer technology used for the planning of dental treatments and to computer software tools for planning an optimised tooth (and soft tissue) set-up for a patient as well as to systems and methods planning an optimised tooth (and soft tissue) set-up for a patient.

BACKGROUND TO THE INVENTION

For dental or orthodontic treatment one or more imaging modalities such as orthopantograms (dental X-ray), computerized tomography (CT) scans or digital photographs are commonly used to analyze, diagnose and document a patient's condition. Recently, digital patient information has also found its way into the planning stage of treatment. Several software solutions exist for simulating dental implant placement in medical (CT) images (SimPlant™, Materialise Belgium), orthodontic treatment can be simulated using digitized information of the patient's dentition (OrthoCAD, Cadent, U.S.; Invisalign, Align Technologies, U.S.) and maxillofacial reconstructions can be planned in a virtual environment (SimPlant CMF, Materialise, Belgium). While these solutions provide powerful tools to the clinician to try out different alternatives at a functional level, the implications of these alternatives at an aesthetical level are generally far from being clear or in some cases disregarded altogether when choosing the clinical approach.

WO2004/098378 and WO2004/098379 describe a workstation for creating a virtual three-dimensional model of a patient using several imaging sources, such as a CT scan, an X-ray and photographs. Software tools allow a trained user to manipulate the model to simulate changes in the position of teeth, such as through orthodontic treatment. The tools described in these documents can be used to plan treatment, and can present a simulation of the outcome of the treatment to a patient. However, as these tools give the user a considerable degree of freedom in the treatment planning, with many decisions to be made by the user, they still require an experienced user to plan the treatment.

Accordingly, the present invention seeks to provide an improved way of planning dental treatments for a patient.

SUMMARY OF THE INVENTION

An object of the present invention is to provide computer based methods and systems for the planning of dental treatments and computer software tools for planning an optimised tooth (and soft tissue) set-up for a patient.

A first aspect of the present invention provides a method for automatic, or semi-automatic, planning of dental treatment for a patient comprising:

(a) obtaining data about an area which is to be treated and data about a face of a patient;

(b) performing a computer-assisted analysis of the data to determine properties of at least the face of the patient; and, (c) creating a modified tooth set-up using a set of stored rules which make use of the determined facial properties.

For the purpose of this application the term 'dental treatment' includes, but is not limited to, prosthetic reconstructions on natural teeth (crown and bridgework, veneers), loose prostheses, prosthetic reconstructions supported by implants, corrections of the soft tissue (i.e. the gums of the patient, mucosa and gingival) and orthodontic treatments, i.e. treatments to correct the position of teeth.

The invention recognises that dental treatment needs to be planned in the context of a patient's face, to provide a result which is aesthetically pleasing as well as being clinically correct. The invention also provides a tool for achieving this, by performing a computer-assisted analysis of facial characteristics, and the use of stored rules to create an optimum tooth and soft tissue set-up. This greatly simplifies the process of creating the modified tooth and soft tissue set-up.

Preferably, the method further comprises generating a three-dimensional representation which simulates the appearance of at least the treatment area with the modified tooth set-up. The three-dimensional representation preferably also simulates the appearance of the patient's face surrounding the treatment area. This allows a patient to view, in advance of the treatment, the post-treatment effects of the modified tooth and soft tissue set-up. Preferably, the three-dimensional representation is as life-like as possible by the use of colour and texture on prosthetic teeth used in the modified set-up. The effect of modified tooth set-up on surrounding facial features (e.g. lips) can also be shown using the three-dimensional representation. This will allow a patient to assess the aesthetical outcome of dental treatment either subsequent to or, more ideally, prior to the selection of the type of clinical treatment. For example, a patient may be offered the choice of a treatment with dental implants, a treatment using crown and bridgework and a treatment using a loose prosthesis and each of these treatment options can be visualised. Such an approach is highly advantageous for the patient, who in an early stage is more involved in the decision making process and is better informed about the aesthetical implications of the different alternatives (e.g. grinding down of teeth vs. implant placement to allow anchoring of a bridge; stripping of the teeth vs. tooth extraction to solve crowding along the dental arch etc.).

The functionality of this invention can be implemented in software, hardware or a combination of these. The invention can be implemented by means of hardware comprising several distinct elements, and by means of a suitably programmed processor. Accordingly, another aspect of the invention provides software comprising instructions (code) which, when executed by a computer or processor, implements the method. The software may be tangibly embodied on an electronic memory device, hard disk, optical disk or any other machine-readable storage medium or it may be downloaded to the computer or processor via a network connection.

A further aspect of the invention provides apparatus for performing the method.

BRIEF DESCRIPTION OF THE DRAWINGS

Embodiments of the invention will be described, by way of example only, with reference to the accompanying drawings in which.

DESCRIPTION OF PREFERRED EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

Figure 1:
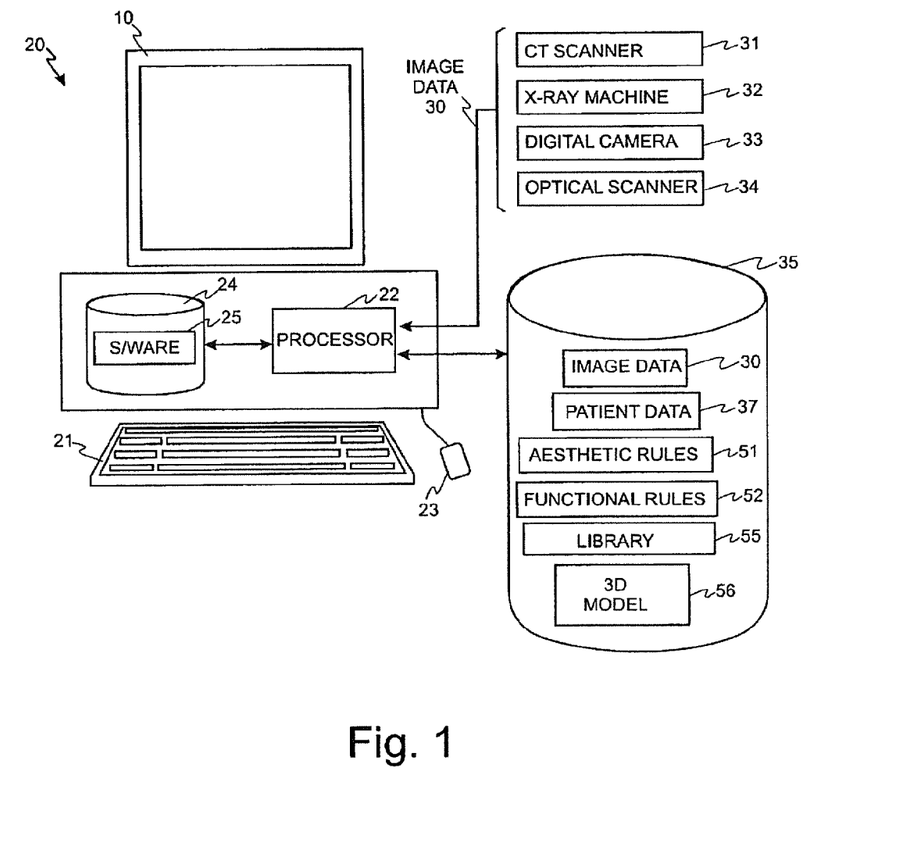
FIG. 1 schematically shows a workstation for implementing the present invention.

FIG. 1 schematically shows a system for implementing an embodiment of the present invention. The system can take the form of a computer workstation 20, such as a general purpose PC, which has a processor 22 and memory/storage 24 and a display 10. Software 25 to implement the invention is stored in memory 24 and executed by the processor 22. A user can interact with the workstation using a keyboard 21, mouse 23 or another input device such as a graphics tablet or an electronic stylus. Workstation 20 receives inputs from a variety of imaging sources, such as a computerized tomography (CT) scanner 31, a dental X-ray machine 32, a digital camera 33 and an optical scanner 34. Each of the imaging sources 31-34 can be manipulated by a user to acquire the image data, and then send this data to the workstation. Alternatively, one or more of the imaging sources 31-34 can be under the control of the workstation 20, with the workstation 20 automatically controlling operation of those imaging sources to acquire the image data. As an example, the workstation 20 can control the digital camera 33 to acquire a picture from each of three predetermined views with respect to the patient. The acquired image data 30 from each imaging source can be stored in the raw form in which it is acquired, or can be processed to convert it into a form in which it can be more readily combined with image data from other sources. This data (in raw or processed format) can be stored 35 within the workstation 20, or externally of the workstation, such as on an external storage device or server which is networked to the workstation 20. Other data 37 about a patient, such as their medical history, can also be stored 35.

The image data 30 that has been acquired from the imaging sources 31-34 is used to generate a virtual, three-dimensional model 56 which is a life-like representation of at least the area of the human body to be treated. Typically, this area will be the patient's jaw, teeth (if any are remaining) and soft tissue surrounding these parts, such as the gums, lips and skin on the outer surface of the face. The extent of the 3D model can be restricted just to the area to be treated and the soft tissue immediately surrounding this area or it can extend to the entire face and head of the user.

Figure 2:
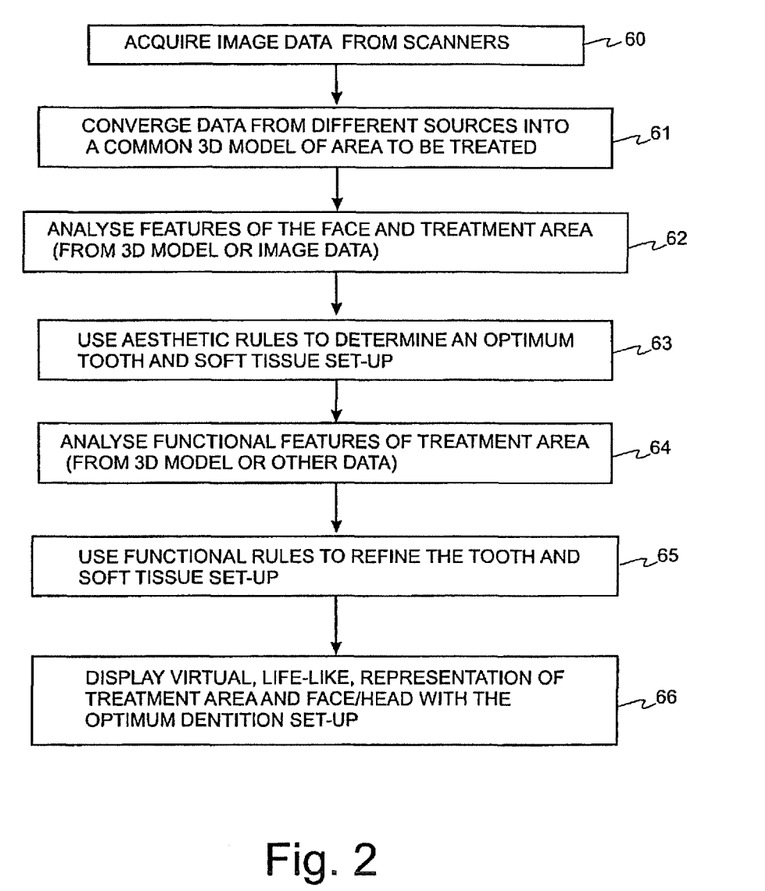
FIG. 2 shows a flow chart of a method according to an embodiment of the present invention.

FIG. 2 shows a flow chart which outlines the main steps of a method of planning treatment in accordance with an embodiment of the invention. Each of the steps will be described in detail.

Acquiring Image Data (Steps 60, 61, FIG. 2)

According to one embodiment of the present invention, the 3D model is created by making 3D measurements of the area to be treated and by converting the measurement data into a digital solid or surface model (for instance, in standard triangulated language [.stl] format). Images from digital 2D or 3D photographs, or from scanned printed photographs, of the same area are then mapped onto this model. A 3D photograph is taken by an optical device that allows capturing the 3D geometry/shape of the object as well as its texture (and optionally colour). In general the device comprises a laser scanner to measure the 3D geometry/shape and a camera for imaging the texture. Both the 3D geometry description and the texture are then combined in one 3D image. A 3D photograph can be taken by a fixed camera or by a moving camera. In the latter case a 3D photograph showing all sides (front, left, back, and right side) of the object is created.

The 3D measurement can be performed directly or indirectly on the area to be treated. A direct measurement can take the form of a CT-scan of the patient, or an optical scan of the head of a patient. A CT-scan gives detail about both soft tissue and bone in a 3D co-ordinate system, by providing a stack of 2D images. Based on these 2D images, a 3D model of the bone or face can be reconstructed. An optical scan of the patient's head can give information about the outer shape and surface features of the face and head. In addition, a small optical scanner can be used to scan the intra-oral region.

An indirect measurement can take the form of an optical scan of a physical replica of the area to be treated, such as a plaster cast manufactured from an impression which has been taken of the area to be treated. Measuring techniques can include, but are not limited to, non-contact scanning using: laser, white light or the like; tactile scanning using a measurement probe; and volumetric scanning such as CT, MRI, μCT, etc. The term 'CT' as used here refers to medical CT scanners where the object remains fixed and the source and detector turn around the object, and results in images with pixel size of about 0.25 min or more. The term 'μCT' refers to non-medical CT scanners where typically the object turns and the source and detector are fixed, and results in images with a typical pixel size 10 to 20 times smaller than that achieved with a CT scan. μCT generally results in more accurate images and can also accurately visualize much smaller details.

Converting the measurement data into a digital model will, depending on the applied measurement technique, involve a series of commonly known data processing techniques such as image segmentation and point cloud meshing. Data derived from different imaging sources (e.g. CT, optical scan . . . ) needs to be combined into a single model. Initially, a separate model is constructed from each image data source (e.g. a model for CT scan data, a model for optical scan data) and the set of individual models is then combined into a single model. One of several known techniques may be used to combine the models:

the 3D models can be registered onto each other by manually translating and/or rotating one of the 3D models with respect to the other. The models are displayed on display 10 of the workstation 20 and an operator manipulates the models.

the 3D models are registered onto each other by indicating corresponding points on both 3D models and applying an N-points registration algorithm. Afterwards an automatic optimization of the registration is possible using a registration optimisation program such as a least-squares registration algorithm.

the 3D models are registered onto each other using a fully automatic registration algorithm based on feature recognition. For example, the registration may be done by a cloud-of-points technique or it may be done by automatically identifying common features in the images.

Such techniques are described, for example, in: P. J. Besl and N. D. McKay, "A method for registration of 3-d shapes", IEEE Trans. Pat. Anal. And Mach. Intel 14(2), pp 239-256, February 1992; R. San-Jose, A. Brun and C.-F. Westin, "Robust generalized total least squares iterative closest point registration", in C. Barillot, D. R. Haynor, and P. Hellier (Eds.): MICCAI 2004, LNCS 3216, pp. 234-241, 2004; A. Gruen and D. Akca, "Least squares 3D surface and curve matching", ISPRS Journal of Photogrammetry and Remote Sensing 59(3), pp 151-174, May 2005.

Photographs (2D or 3D) can be scaled to a required dimension using one of several techniques:

a calibration piece, i.e. a piece with exactly known geometric dimensions, can be added in the field of view of the camera while taking photographic images of the patient. This allows exact scaling of the photographs afterwards.

measurements can be performed on photographs and 3D models by using anatomical reference distances (e.g. interpupillary distance . . . ) to determine the scale factor for the photographs.

The scaling can be done automatically by automatically detecting reference points or features in the images and scaling these to match each other.

For mapping of the 2D or 3D photographs onto the digital model one of several techniques may be used when photographs and digital models contain identical surfaces (e.g. teeth visible in photograph, facial skin . . . ):

Manual registration: The photograph is aligned with the digitized treatment area. The photograph can be scaled and translated. The 3D representation of the treatment area can be rotated. The user rotates the representation to adapt its orientation to match the angle under which the photograph was made. The size of the photograph is adjusted and the image is translated until it is aligned with the view on the 3D representation. The steps are repeated to tune the registration.

Semi-automatic registration: The user rotates the representation to adapt its orientation to match the angle under which the photograph was taken. Photograph and 3D representation are shown side-by-side. Reference points are indicated on both to mark corresponding features. A final mapping is performed either by: a least-squares algorithm/n-point registration/ICP (Iterative Closest Point) registration, which will find the optimal transformation necessary to align both sets of points; or by an exact matching at the location of the reference points and minimal deformations in between, using an RBF (radial base functions) optimization approach.

Automatic registration: Registration applying feature recognition.

Figure 3:
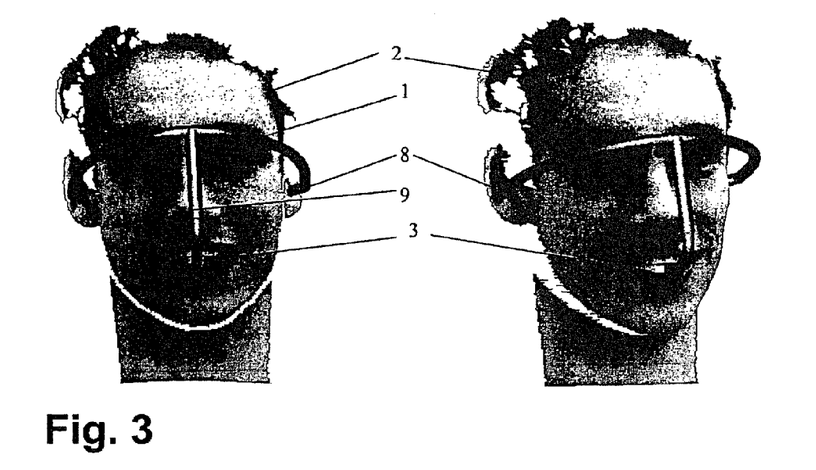
FIG. 3 shows one way of registering a 3D photograph and digitised plaster casts using a face bow.

In a case where no identical surfaces are available (e.g. mapping of 2D or 3D photograph of edentulous patient onto digitized 3D models of the maxillar and mandibular plaster casts) the above-mentioned registration techniques cannot be used. In these cases a preferential approach makes use of face bow measurements to map the different data sets. Referring to FIG. 3, a face bow is a mechanical device used in dentistry to record the positional relations of the maxillary arch to the temporomandibular joints, and to orient dental casts in this same relationship to the opening axis of the mechanical articulator. A face bow consists of two metal parts attached together. The first part 3, called the bite fork, is shaped like a horseshoe and is inserted in the mouth of the patient and clamped between upper and lower jaw. The second part comprises two curved elements 1, 9. The ends 8 of the first curved element 1 are positioned in the ear channels of the patient. The second curved element 9 forms a nasal guide that is put in contact with the nose of the patient. The bite fork 3 is fixed to the second curved element 9. The current position of all parts of the face bow is maintained and then used to transfer the plaster cast into the corresponding mechanical articulator. This implies that the face bow used for transfer of the occlusion from the patient's mouth to the mechanical articulator is now virtually created and positioned onto the 3D photograph of the patient (FIG. 3). The bite registration 3 is also digitized and used to register the digital 3D models of the patient's jaws in the same coordinate system as the 3D photograph. In case of 2D photographs, a virtual face bow cannot be used and a preferential method in this case is using the default values (as used in a mechanical articulator) to position the 3D models of the patient's jaws in correct relation to the intercondylar axis, which can be defined onto the 2D photograph of the patient's face.

As an alternative to the above described method, a three-dimensional model of the area to be treated can be built directly from a 2D video sequence, such as by matching objects and features appearing in images which have been acquired from different viewpoints. Since the video data inherently holds information that can be related to more than mere spatial coordinates of the captured points, but also to color, texture, etc. the calculated reconstruction can be made to reflect each of these qualities, thereby achieving a life-like model.

The composite 3D model created at step 61 should preferably include the face of the patient to allow facial analysis to be based on the model. The 3D model used to plan a modified tooth set-up does not have to be life-like, but this information is useful to visualize to the user and patient the effects of the treatment and can be rendered in the final stage 66 of the method when a virtual representation of the tooth set-up following treatment is displayed to a user and a patient.

Facial Analysis (Steps 62, 63, FIG. 2)

Figure 4:
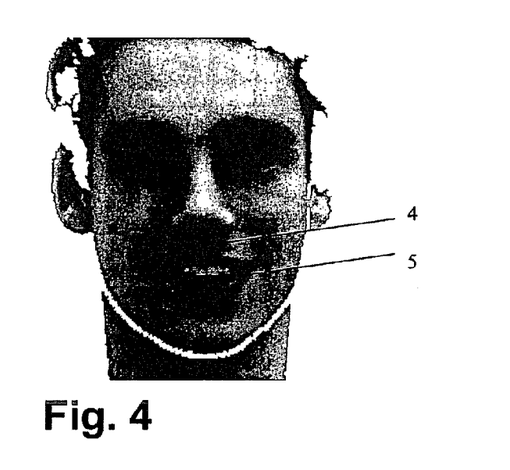
FIG. 4 shows an example of an aesthetical rule in which the width of maxillary incisors should be equal to the width of the nose base.
Figure 5:
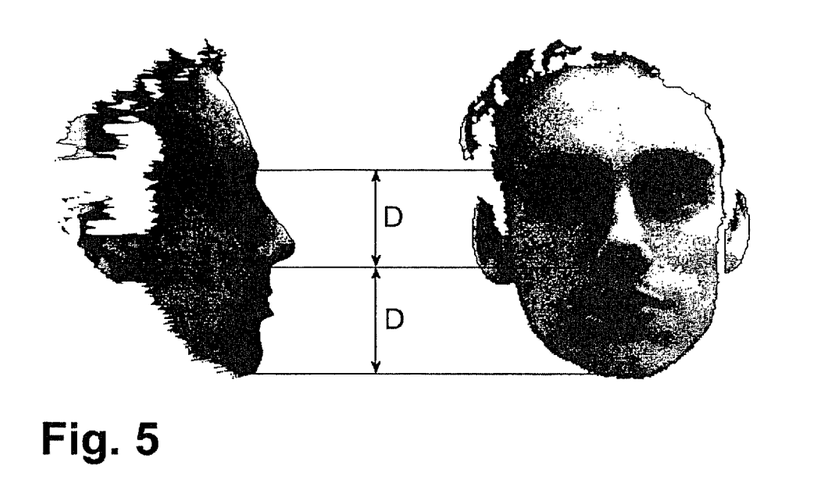
FIG. 5 shows an example of an aesthetical rule in which the distance between eyebrow and nose base should be equal to distance between nose base and top of chin during occlusion.
Figure 6:
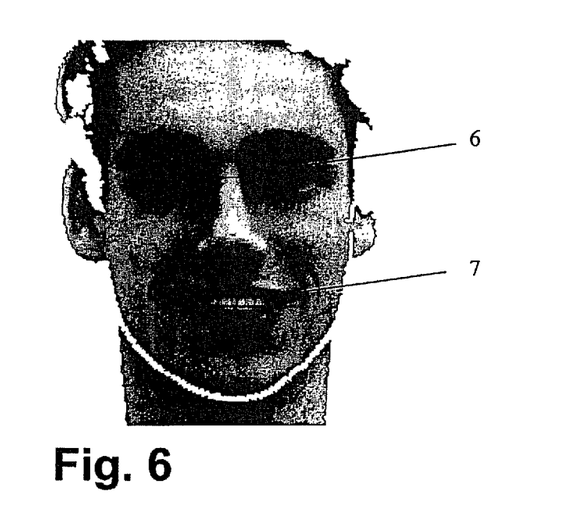
FIG. 6 shows an example of an aesthetical rule in which the occlusal plane or the line connecting the cusps of the maxillar canines should be parallel to the interpupillary line.

According to one embodiment of the invention the 3D model of the patient, which has been created in one of the ways described above, is analysed to determine information about the aesthetical appearance of the face and/or of the area to be treated. This analysis can be fully automatic, or semi-automatic. In a semi-automatic analysis, the computer program prompts the user to indicate certain anatomical points and/or lines on the face of the patient, which are needed for the facial analysis. The user marks these points on the graphical representation of the face by using an input tool such as a mouse 23, keyboard 21, graphics tablet, electronic stylus etc. The program then performs facial analysis based on measurements between these marked points and automatically creates or modifies the tooth set-up as described below. The following table, and FIGS. 4-6, show some example anatomical points which the program can prompt a user to mark. Even in the semi-automatic embodiment, the program can be arranged to automatically determine some of the facial features without any user prompting and input such as, for example, the overall shape of a patient's face (rule A) and the interpupillary line (rule D).

A set of general aesthetical rules use the results of the facial analysis to create an aesthetically optimal dental configuration or tooth set-up, based on the particular characteristics of the patient's face. The following table gives a non-exhaustive list of fourteen possible facial analyses and corresponding rules:

| | Aesthetical analysis | Aesthetical rule |
|---|---|---|
| A | Determine the shape of the patient's face and, if available, the patient's teeth. Three main facial shapes exist: (i) rectangular or square shaped. A rectangular or square shaped face has substantially the same width at the forehead and just below the cheekbones; (ii) tapered, A tapered face is wide at the forehead and narrows to a small delicate chin; (iii) oval. An oval face is slightly wider at the cheekbones than at the forehead or jaw-line. Teeth are classified in three different shapes: tapered, ovoid, and square-shaped. If a patient has any remaining teeth, the shape of the teeth can be determined based on the digitized information of the patient's remaining dentition. | The optimal tooth shape is selected according to the following rules: (1) In partially edentulous cases (i.e. the patient has some teeth remaining) the tooth shape is determined based on the shape of the remaining natural teeth and/or the shape of the patient's face. (2) In edentulous cases the tooth shape is chosen based solely on the analysis of the shape of the patient's face. A rectangular or square shaped face corresponds with square-shaped teeth. A tapered face corresponds with tapered-shaped teeth. An oval face corresponds with ovoid-shaped teeth. |
| B | Determine the width of the nose base (see 4, FIG. 4). | Design or reshape the four maxillar incisors so that their total width (5, FIG. 4) is approximately equal to the width of the nose base (Gerber). |
| C | Determine the distance between eyebrow and nose base (see FIG. 5). | Position the occlusal plane relative to the patient's face so that the distance between the nose base and the top of the chin during occlusion is equal to said distance between eyebrow and nose base. |
| D | Determine the interpupillary line, i.e. the line connecting the centre of the eyes (6, FIG. 6). | Reconstruct or correct the teeth so that the occlusal plane or the line connecting the cusps of the maxillar canines (7, FIG. 6) is parallel to said interpupillary line. |
| E | Determine the symmetry line of the face, i.e. the line from the centre of the forehead along the subnasal point to the centre point of the chin. | Angulate or reorient the frontal maxillar incisors so that their facial axis is parallel to said symmetry line and position the central incisors so that their contact point lies on said symmetry line. |
| F | Determine the nasio-labial angle, i.e. the angle between the columella of the nose and the anterior surface of the upper lip measured in a sagittal (lateral) view of the patient's face. | Reconstruct or correct the maxillar incisors so that the nasio-labial angle is approximately 90°. Therefore a soft tissue simulation is needed to predict the tooth position for the upper lip position, more particular with a nasio-labial angle of 90°. |
| G | Determine in a sagittal (lateral) view of the patient's face the distance of the upper and lower lip to the line through the tip of the nose and the chin. | Reconstruct or correct the teeth so that the distance of upper lip to said line is 4 mm and the distance of lower lip to said line is 2 mm. |
| H | Determine the position of the upper lip while smiling. | Position or correct the frontal maxillar teeth so that only one quarter of their height is covered by the upper lip while smiling. For some patients the smile-line, i.e. the borderline of the upper lip during normal smiling, is much higher than ideally, and the upper gum is exposed. In these cases a gingival correction is needed to allow implant placement in the frontal maxilla. Without gingival correction pink porcelain will be needed in the prosthetic reconstruction and this is not compatible with the necessary interdental spaces for cleaning purposes of the implants. |
| I | Determine the curve formed by the lower lip while smiling | Position or correct the frontal maxillar teeth so that their incisal edge is parallel to said curve and just touching the lower lip or showing a slight gap. |

Figure 7:
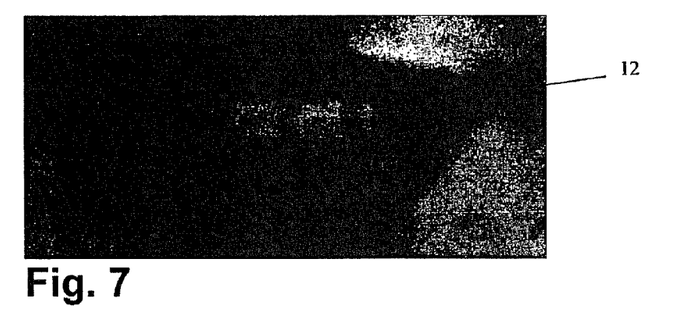
FIG. 7 shows buccal corridors during smiling.

| | Aesthetical analysis | Aesthetical rule |
|---|---|---|
| J | Determine the buccal corridor, i.e. the small space visible between the angles of the mouth and the teeth, during smiling (12, FIG. 7). | Determine or adapt the maxillar dental arch shape as well as the orientation of maxillar premolars and molars to obtain a normal size of said buccal corridor. A too wide dental arch will result in no buccal corridor while a too small dental arch will result in a buccal corridor that is too prominent. |
| K | Determine the width to height ratio of the maxillar central incisors. | Adapt the maxillar central incisors if needed to approximate the ideal value of 80% for the width to height ratio. |
| L | Determine the proportion of maxillar central incisor width to lateral incisor width to canine width. | Adapt maxillar incisors and canines if needed to obtain the ideal width proportion of 1.6, 1, and 0.6 respectively. |
| M | Determine the position of the upper lip during talking. | Adapt the position or size of the maxillar incisors to obtain a visibility of approximately 1.5 mm of said teeth during talking. |
| N | Determine the overjet of the teeth in a sagittal (lateral) view. | Incline or adapt the inclination of the frontal teeth to obtain an overjet value used in common practice, i.e. 2 mm. |

The analyses listed above fall into the broad categories of: aesthetic characteristics of the patient's face, including measurements between facial features (A-G); aesthetic characteristics of the face which may be determined by the underlying jaw and teeth (H, I, J, M) and aesthetic characteristics of the patient's teeth (K, L, N). The analysis of aesthetic features can be performed on the virtual model 56 of the patient, or on some of the image data 30 of the patient, such as photographs of the patient's face and teeth.

Functional Analysis (Steps 64, 65, FIG. 2)

In addition to making an analysis of the aesthetic properties of the patient, the analysis can be extended to include a computer-assisted analysis of more 'functional' characteristics of a patient. Functional information resulting from this analysis can be used in a set of functional rules which can adapt the dental configuration derived at step 63, FIG. 2. Alternatively, the dental configuration may be directly based on a combined set of aesthetic and functional rules which make use of both the aesthetic and functional information.

Figure 8:
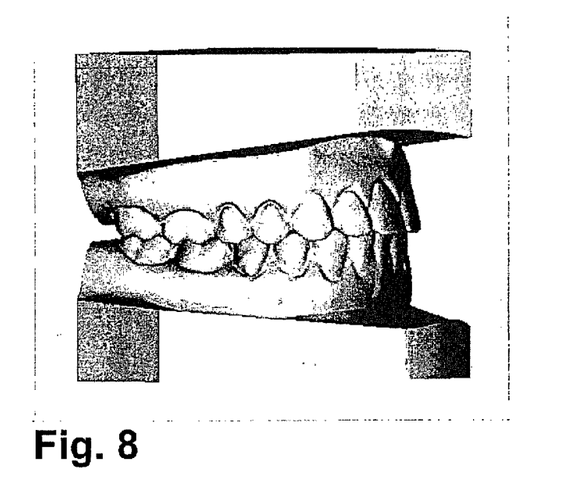
FIG. 8 shows an example of a class 1 molar relationship.

The following table gives a non-exhaustive list of functional analyses and corresponding rules:

| Functional analysis | Functional rule |
|---|---|
| Determine class (I, II, or III) of molar relationship. (i) Class I malocclusion refers to a malocclusion in which the buccal groove of the mandibular first permanent molar occludes with the mesiobuccal cusp of the maxillary first permanent molar. (ii) Class II malocclusion refers to a malocclusion in which the buccal groove of the mandibular first permanent molar occludes posterior (distal) to the mesiobuccal cusp of the maxillary first permanent molar. (iii) Class III malocclusion refers to a malocclusion in which the buccal groove of the mandibular first permanent molar occludes anterior (mesial) to the mesiobuccal cusp of the maxillary first permanent molar. | Ideally, a class I molar relationship (FIG. 8) should be created. But, if a patient has, for instance, class II/III molar relationships at the left side, then the right side can be reconstructed mimicking the class II/III molar relationships. |
| Determine crown angulation of remaining teeth. | Mimic crown angulation of remaining teeth in prosthetic reconstruction. If no remaining teeth, use average values for the angulation of the crowns. |
| Determine crown inclination of remaining teeth | Mimic crown inclination of remaining teeth in prosthetic reconstruction. If no remaining teeth, use average values for the inclination of the crowns. |
| Determine dental arch for upper and lower jaw based on remaining teeth or for edentulous cases based on average curves and the jaw information (Staub . . .). | Align crowns tangent to determined dental arch. |
| Determine midline of dental arches (upper and lower). | Adapt dental arches until these midlines match. |

| Functional analysis | Functional rule |
| --- | --- |
| Determine contact between neighboring teeth. | Mimic contact of remaining teeth. If edentulous position crowns in tight contact to neighbors. |
| Determine contact points during movement of the jaws. | Adapt occlusal surfaces of the crowns to obtain an ideal articulation. |
| Determine overjet. | Adapt tooth position or reconstruct crown to obtain optimal value of 2 mm. |
| Determine overbite. | Adapt tooth position or reconstruct crown to obtain optimal value of 2 mm. |

Functional analysis is not limited to optimal tooth contacts but can in a broader sense include phonetics and biomechanics (e.g. optimal tooth loading).

The computer-assisted functional analysis can include identification of ideal tooth contact points and can be performed by means of digitized information of static and dynamic check bites of the individual patient or by means of a virtual articulator. An articulator is a mechanical instrument which is used to examine the static and dynamic contact relationships between the occlusal surfaces of both dental arches. It represents the human temporomandibular joints and jaws, to which maxillary and mandibular casts may be attached in order to simulate some or all mandibular movements. Different settings regarding the jaw morphology and mandibular movement can be adjusted on an articulator. Those values are set using patient-specific data or average values known in literature. A virtual articulator establishes the static and dynamic contact relationships in a virtual environment. It simulates forward, backward, left lateral, right lateral, opening and closing mandibular movements as constrained by the geometric restrictions imposed by settings using patient-specific data or average values known in literature. Moreover, a virtual articulator calculates and visualizes the resulting occlusal contacts. Alternatively jaw movement and occlusal contacts can be recorded and provided as a 3D path relative to known landmarks on the patient.

Figures 9A, 9B:
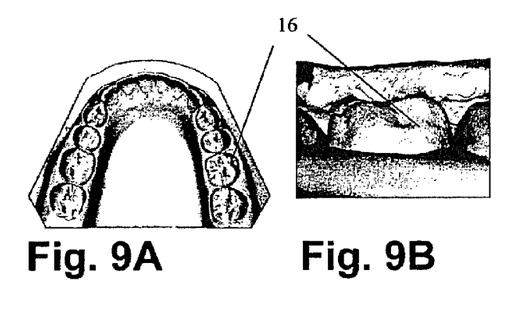
FIGS. 9A-9C show an example of modifying the functional properties of a prosthetic tooth.
Figure 9C:
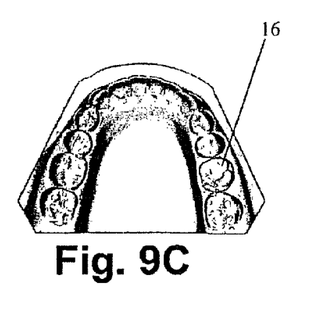

FIGS. 9A-9C illustrate one example of how the functional characteristics of a set-up are determined and modified. FIG. 9A shows a proposed tooth set-up resulting from facial analysis and application of the aesthetic rules. This has resulted in a prosthetic tooth 16 being inserted into a modified set-up. Initially the tooth 16 has a default shape and surface features, such as the default properties of an element in the library 55 of elements. In FIG. 9B the occlusal surface of the new tooth 16 is analysed with respect to antagonists (e.g. the teeth shown directly above tooth 16). As a result of the analysis, the outer surface of the tooth 16 is modified to present a better occlusal surface. FIG. 9C shows the result of the optimization.

Each of the functional and aesthetical rules can be assigned a weighting factor to more, or less, profoundly influence their impact on the final dentition. Each weighting factor can have a value based on past experience. Alternatively, each weighting factor can be adjusted by the team treating the patient, in accordance with their expertise on a case-by-case basis. The following is a practical example of how the weighting factors can be used. Suppose a tooth set-up must be created for a patient missing the four maxillar incisors and both canines. Aesthetical rule L predicts the ideal proportion for the widths of the missing teeth. Aesthetical rule B predicts the total width of the four maxillar incisors based on the width of the nose base of the patient. If the patient has a very small nose then rule L should be determining for the final width of the teeth, so rule L must have a higher weighting factor than rule B. This will result in a normal proportional width of the missing teeth in between the remaining maxillary first premolars. If, in this case, rule L would have been given a much lower weighting factor than rule B, then very small maxillar incisors would be created in combination with very thick canines to be able to fill the gap in between the remaining maxillary first premolars. So the ideal proportion would not be respected and would result in a less aesthetical outcome.

Figure 10:
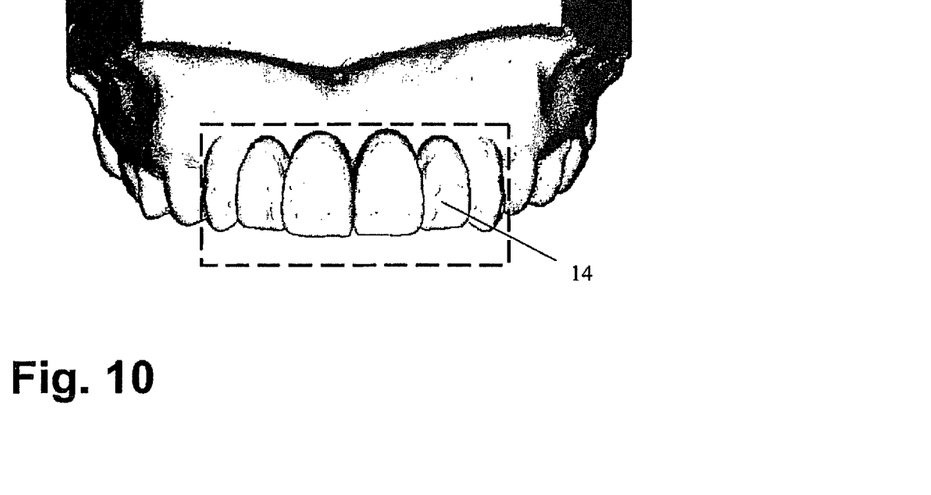
FIG. 10 shows the reconstruction of missing teeth by means of library teeth.

The process of generating an optimal tooth (and soft tissue) set-up can be achieved in different ways:

- a tooth (and soft tissue) set-up can be optimized with respect to all, or only some, aesthetical rules in an iterative process;
- a tooth (and soft tissue) set-up can be determined as the weighted average of all, or some, aesthetical rules with weighting factors representing, for example, the importance of the aesthetical rules to achieving an optimal set-up;
- a tooth (and soft tissue) set-up can be determined using a first sub-set of rules and then optimized using a second sub-set of the rules.

Where a patient has a partial set of teeth, the invention can generate an optimal dental configuration which virtually models replacement teeth in the places where the patient is currently missing teeth. The replacement teeth are selected in accordance with the aesthetic and functional rules. FIG. 10 shows an example where a group of six prosthetic teeth 14 have been inserted into a model of a patient's jaw.

Figure 11:
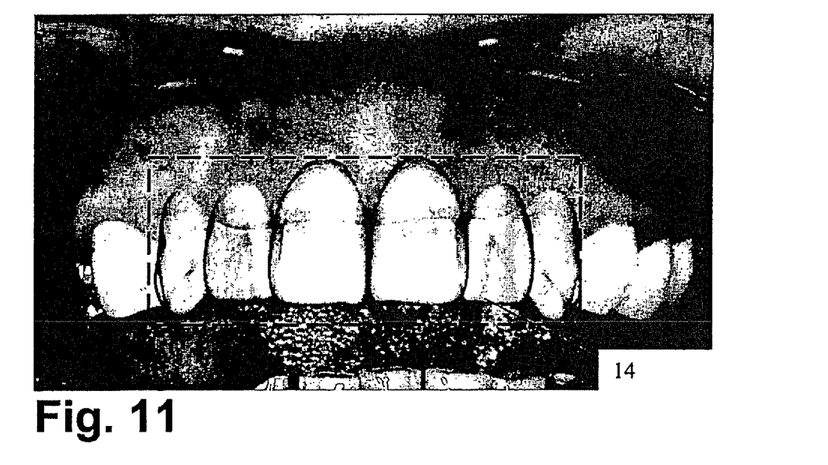
FIG. 11 shows the application of texture to library teeth to give a life-like representation of reconstructed teeth.
Figure 12:
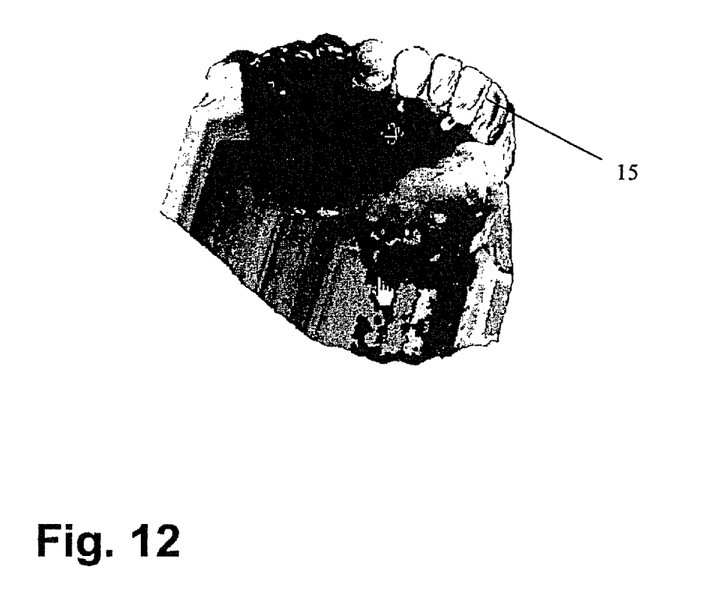
FIG. 12 shows an alternative view of reconstructed teeth.

Additionally, it may be desirable to reposition some of the patient's existing teeth. This can also be modelled, and the results of the repositioning can be displayed to the patient. A library 55 stores individual teeth (of varying type, shape and size) and complete or partial set-ups, for use with patients who are fully or partially edentulous. Each of the library set-ups can be adapted in accordance with the aesthetic (and functional) rules, or the software may select the best of the library set-ups based on the aesthetic (and functional) rules. The digital library 55 of elements can have a default set of predefined properties such as colour, texture etc. to give them a life-like appearance. Alternatively, such information may be mapped onto a 'plain' element to obtain a desired life-like appearance. A selection of options can, for example, be presented to a user in the form of a menu offering a palette of colours and textures. FIG. 11 shows the model of FIG. 10 following the application of colour and texture to library elements 14 and FIG. 12 shows another life-like representation of a treatment area with prosthetic teeth to which colour and texture have been applied.

The virtual modeling may be performed by user interaction in the digital environment. Software 25 executed by the workstation creates a graphical user interface on display 10 which allows a user to make select, introduce, position, reposition or modify individual teeth or groups of teeth in an automatic or semi-automatic manner. The software can include routines which automatically position teeth along a predefined arch, or routines for automatically positioning teeth in function of occlusion relative to the antagonist dentition. Alternatives for orthodontic cases are tooth extraction, widening of the jaw and stripping (i.e. reducing the width) of teeth. The occlusal surface of already positioned teeth may also be modified using the software tools.

Virtual Representation of Treatment Area, Post-Treatment (Step 66, FIG. 2)

The final step of the method displays a virtual representation of the treatment area, displaying the effect of the optimal tooth (and soft tissue) set-up. It is likely that there will be a range of possible treatment options. As an example, for dental restorations alternative treatment options can include different tooth morphologies, sizes and colours. Each of the treatment options can be presented to a user and a patient and the patient will be able to view the aesthetic results of the treatment. In a particular embodiment, the virtual representation can be modified to simulate different facial expressions, such as smiling. Step 66 can use the same 3D model as was created at step 61, FIG. 2, and updated to include the treatment work determined at step 65, FIG. 2. The modified tooth set-up determined at step 65 can be used to update a life-like representation of the area to be treated. The update consists of spatially matching the life-like representation of the treatment area and the modified tooth set-up and visualizing them simultaneously on a display 10. Spatially matching refers to registering both entities. For instance when only a 2D photograph of the patient is available then the optimal tooth set-up should be positioned, oriented, and scaled relative to the 2D photograph and then embedded within the photograph to visualize the result. Alternatively, elements (for example, teeth) may be removed from the 3D life-like representation of the treatment area and replaced by corresponding counterparts in the generated set-up. Updating the life-like representation implies calculating the effect of the generated optimal tooth (and soft tissue) set-up on the position, inclination and/or deformation of the entire or local regions of the treatment area. The treatment area is modified accordingly. One example pertains to the way in which the lips are supported by the teeth. Modifying the inclination of the teeth will also change the position of the lips.

In a further embodiment of invention the computer assisted facial analysis can result in quantitative and qualitative (textual) guidelines, which are subsequently used by a dental technician to create the optimal tooth set-up manually. Afterwards, the created tooth set-up (wax-up) can be scanned and converted to a 3D model so a composite 3D image representation can be created to show the effect of the new set-up on the patient's face.

ILLUSTRATIVE EXAMPLES

Example 1

A 3D photograph, or a set of 2D photographs, are taken of the face (while smiling) of a patient needing orthodontic treatment. Also, impressions of the patient's dentition are taken in alginate or silicon material. Using these impressions, plaster models of the intra-oral anatomy of the patient are manufactured. The plaster models are subsequently digitized using an optical scanner in order to yield a virtual 3D model that represents the dentition of the patient prior to treatment. In software, the virtual 3D model of the patient's dentition is registered onto the 3D photograph of the patient's face to create a life-like representation. The plaster casts contain the information of the gums and the 3D photograph contains the surface information of the patient's face. Computer-assisted facial and functional analyses are performed and the results of these analyses are used in a set of rules to establish an optimum dentition for the patient. Adapting position, inclination, and angulation of the patient's natural teeth in accordance to the rules creates the optimal tooth set-up. If necessary, natural teeth presently sited in the patient's jaw can be extracted virtually to obtain an optimized diagnostic tooth set-up. Finally the optimal tooth set-up is visualized together with the patient's 3D photograph.

Example 2

A 2D photograph, a CT scan and impressions are taken of a partially edentulous patient needing a prosthetic reconstruction. A virtual, life-like, representation of the patient is created by mapping the 2D photograph onto the 3D soft tissue model of the patient's face generated from the CT images and registering the 3D models of the patient's dentition generated from μCT images of the impressions with the CT images of the patient's face. Replacement teeth are selected for the sites where the patient is currently missing teeth. The replacement teeth are selected by performing the facial/aesthetic analysis and following the aesthetical and functional rules, so as to match the shape of the remaining dentition of the patient. The software can select the replacement teeth automatically from a library of teeth, and place these in the virtual model of the patient's mouth, or the software can suggest a selection of suitable teeth on the basis of the aesthetical information and the rules. A user can then use their judgement to select the best replacement teeth from those suggested by the software, and place these within the virtual model of the jaw. Then, the occlusal surfaces of these library teeth are functionally optimized based on the functional rules and the results of the computer-assisted functional analysis.

Example 3

A 3D photograph and impressions are taken of a fully edentulous patient. Scanning these impressions via μCT and performing image processing (segmentation, 3D model creation, surface inversion etc.) yields a digital representation of the intra-oral anatomy of the patient. Positioning the virtual 3D models of the patient's edentulous jaws relative to the 3D photograph using face bow measurements creates the virtual, life-like, representation. Then, an initial tooth set-up is created from library teeth by using statistical information (e.g. Staub pentagram, average shape of dental arch) as well as rules established by the computer assisted facial analysis. A computer-assisted functional analysis is performed for this initial diagnostic set-up taking into account patient specific parameters for setting the virtual articulator. The occlusal surfaces of these library teeth are optimized functionally to obtain optimal occlusion and articulation. The optimization process is iterated until the best compromise is found between functional and aesthetical considerations.

The invention is not limited to the embodiments described herein, which may be modified or varied without departing from the scope of the invention.

The invention claimed is:

1. A method for automatic, or semi-automatic, planning of dental treatment for a patient comprising:
    (a) obtaining data about an area which is to be treated and data about a face of a patient;
    (b) performing a computer-assisted analysis of the data to determine properties of at least the face of the patient;

(c) creating a modified tooth set-up using a set of stored rules for placing, moving, or modifying at least one tooth in a mouth of the patient which make use of the determined facial properties selected:

1) wherein when aesthetic characteristics of the patient's face, determined by measurements between facial features, is selected, the rules are selected from the group consisting of:
   A) selecting an optimal tooth shape by:
      in partially edentulous cases, wherein the patient has some teeth remaining, a tooth shape is determined based on a shape of the remaining natural teeth, a shape of the patient's face, or a shape of the remaining natural teeth and the shape of the patient's face, or
      in edentulous cases the tooth shape is chosen based solely on the analysis of the shape of the patient's face, or
      a rectangular or square shaped face corresponds with square-shaped teeth, or
      a tapered face corresponds with tapered-shaped teeth, or an oval face corresponds with ovoid-shaped teeth;
   B) design or reshape four maxillar incisors of the patient so that their total width is approximately equal to the width of a nose base;
   C) position an occlusal plane relative to the patient's face so that the distance between the nose base and the top of the patient's chin during occlusion is equal to said distance between eyebrow and nose base;
   D) reconstruct or correct the teeth so that the occlusal plane or the line connecting cusps of the patient's maxillar canines is parallel to an interpupillary line;
   E) angulate or reorient the frontal maxillar incisors so that their facial axis is parallel to a symmetry line and position the central incisors so that their contact point lies on said symmetry line;
   F) reconstruct or correct the maxillar incisors so that a nasio-labial angle is approximately 90°, wherein a soft tissue simulation is needed to predict the tooth position for the patient's upper lip position; and
   G) reconstruct or correct the teeth so that the distance of upper lip to said line is 4 mm and the distance of lower lip to said line is 2 mm;

2) wherein when aesthetic characteristics of the face determined by the underlying jaw and teeth is selected, the rules are selected from the group consisting of:
   H) position or correct the frontal maxillar teeth so that only one quarter of their height is covered by the upper lip while smiling, wherein in cases where a smile-line created at a borderline of the upper lip during normal smiling exposes the upper gum, a gingival correction is used to allow implant placement in the frontal maxilla;
   I) position or correct the frontal maxillar teeth so that their incisal edge is parallel to said curve and lust touching the patient's lower lip or showing a slight gap;
   J) determine or adapt a maxillar dental arch shape as well as the orientation of maxillar premolars and molars to obtain a normal size of a buccal corridor, wherein a too wide dental arch will result in no buccal corridor while a too small dental arch will result in a buccal corridor that is too prominent; and
   M) adapt the position or size of the maxillar incisors to obtain a visibility of approximately 1.5 mm of said teeth during talking; and 3) wherein when aesthetic characteristics of the patient's face determined by the teeth is selected, the rules are selected from the group consisting of:
   K) adapt the maxillar central incisors to approximate the ideal value of 80% for the width to height ratio;
   L) adapt maxillar incisors and canines to obtain the ideal width proportion of 1.6, 1, and 0.6 respectively;
   and
   N) incline or adapt the inclination of the frontal teeth to obtain an overjet value used in common practice.

2. The method according to claim 1 further comprising generating a three-dimensional representation which simulates the appearance of at least the treatment area with the modified tooth set-up.

3. The method according to claim 2 wherein the step of generating a three-dimensional representation also simulates the appearance of the patient's face surrounding the treatment area.

4. The method according to claim 1 wherein the step (b) of performing a computer-assisted analysis of the data also determines properties of existing teeth and step (c) creates a modified tooth set-up using a set of rules which make use of the determined facial properties and the existing teeth of the patient, or
   wherein the analysis at step (b) comprises determining a shape of the patient's face and step (c) comprises selecting a shape of prosthetic teeth on the basis of the determined shape, or
   wherein the analysis at step (b) comprises determining distance between features of the patient's face or an alignment of features of the patient's face and step (c) comprises modifying the tooth set-up based on the determined distance or alignment, or
   wherein the analysis at step (b) comprises determining an interpupillary line and step (c) comprises reconstructing teeth, or correcting the position of the teeth, so that an occlusal plane or a line connecting the cusps of the maxillar canines is parallel to the determined interpupillary line, or
   wherein the analysis at step (b) comprises determining the position of the patient's lip and step (c) comprises modifying the tooth set-up based on the determined position, or
   wherein the facial analysis at step (b) comprises determining the position of the patient's upper lip while smiling and step (c) comprises positioning frontal maxillar teeth so that only one quarter of their height is covered by the upper lip while smiling.

5. The method according to claim 1 wherein step (c) comprises generating a three-dimensional model of the area to be treated from the obtained data and creating a modified tooth set-up on the model.

6. The method according to claim 1 wherein the step of performing a computer-assisted analysis of the data comprises prompting a user to indicate the position of anatomical points on a two-dimensional or three-dimensional representation of the face of the patient and automatically determining facial properties based on inputs received from a user.

7. The method according to claim 1 further comprising determining functional data of the area to be treated or the modified set-up and step (c) uses the functional data.

8. The method according to claim 7 wherein the functional data concerns an occlusion or articulation of the area to be treated or the modified tooth set-up.

9. The method according to claim 8 wherein the step of determining functional data comprises determining optimum tooth contact points and step (c) comprises modifying the tooth set-up to optimise tooth contact points.

10. The method according to claim 9 wherein the data obtained at step (a) is used to generate a three-dimensional model of the patient and the determination of tooth contact points uses the model or
wherein the data obtained at step (a) is used to generate a three-dimensional model of the patient and the facial analysis of step (b) uses the model.

11. The method according to claim 1 wherein the set of rules used in step (c) are weighted.

12. The method according to claim 11 wherein the set of rules used in step (c) are weighted according to their relative importance for optimizing the tooth set-up.

13. The method according to claim 1 wherein the data about a face of a patient comprises one or more of: a 2D photograph; a 3D photograph; and an optical scan of an external surface of at least part of the patient's head.

14. The method according to claim 1 wherein the data about an area to be treated comprises data acquired using a plurality of different imaging techniques.

15. The method according to claim 14 wherein the imaging techniques comprise at least one of: a 2D photograph; a 3D photograph; an intra-oral optical scan; an X-ray; or a computed tomography scan.

16. The method according to claim 14 wherein step (c) comprises correlating the data acquired using different imaging techniques to generate a three-dimensional model of the patient's jaw and existing teeth, or
wherein step (c) further comprises allowing a user to manipulate the modified tooth set-up via a graphical user interface or
wherein step (c) further comprises accessing a library of elements and using the library to create the modified tooth set-up.

17. Apparatus for automatic, or semi-automatic, planning of dental treatment for a patient, the apparatus comprising:
an input for receiving data about an area which is to be treated and data about a face of a patient; and
a processor comprising non-transitory computer readable medium, which when executed is configured to:
perform a computer-assisted analysis of the data to determine properties of at least the face of the patient; and
create a modified tooth set-up using a set of stored rules for placing, moving, or modifying at least one tooth in a mouth of the patient which make use of the determined facial properties selected:
1) wherein when aesthetic characteristics of the patient's face, determined by measurements between facial features, is selected, the rules are selected from the group consisting of:
A) selecting an optimal tooth shape by:
in partially edentulous cases, wherein the patient has some teeth remaining, a tooth shape is determined based on a shape of the remaining natural teeth, a shape of the patient's face, or a shape of the remaining natural teeth and the shape of the patient's face, or
in edentulous cases the tooth shape is chosen based solely on the analysis of the shape of the patient's face, or
a rectangular or square shaped face corresponds with square-shaped teeth, or
a tapered face corresponds with tapered-shaped teeth, or an oval face corresponds with ovoid-shaped teeth;
B) design or reshape four maxillar incisors of the patient so that their total width is approximately equal to the width of a nose base;
C) position an occlusal plane relative to the patient's face so that the distance between the nose base and the top of the patient's chin during occlusion is equal to said distance between eyebrow and nose base;
D) reconstruct or correct the teeth so that the occlusal plane or the line connecting cusps of the patient's maxillar canines is parallel to an interpupillary line;
E) angulate or reorient the frontal maxillar incisors so that their facial axis is parallel to a symmetry line and position the central incisors so that their contact point lies on said symmetry line;
F) reconstruct or correct the maxillar incisors so that a nasio-labial angle is approximately 90°, wherein a soft tissue simulation is needed to predict the tooth position for the patient's upper lip position; and
G) reconstruct or correct the teeth so that the distance of upper lip to said line is 4 mm and the distance of lower lip to said line is 2 mm;
2) wherein when aesthetic characteristics of the face which may be determined by the underlying jaw and teeth is selected, the rules are selected from the group consisting of:
H) position or correct the frontal maxillar teeth so that only one quarter of their height is covered by the upper lip while smiling, wherein in cases where a smile-line created at a borderline of the upper lip during normal smiling exposes the upper gum, a gingival correction is used to allow implant placement in the frontal maxilla;
I) position or correct the frontal maxillar teeth so that their incisal edge is parallel to said curve and just touching the patient's lower lip or showing a slight gap;
J) determine or adapt a maxillar dental arch shape as well as the orientation of maxillar premolars and molars to obtain a normal size of a buccal corridor, wherein a too wide dental arch will result in no buccal corridor while a too small dental arch will result in a buccal corridor that is too prominent; and
M) adapt the position or size of the maxillar incisors to obtain a visibility of approximately 1.5 mm of said teeth during talking; and
3) wherein when aesthetic characteristics of the patient's face determined by the teeth is selected, the rules are selected from the group consisting of:
K) adapt the maxillar central incisors to approximate the ideal value of 80% for the width to height ratio;
L) adapt maxillar incisors and canines to obtain the ideal width proportion of 1.6, 1, and 0.6 respectively; and
N) incline or adapt the inclination of the frontal teeth to obtain an overjet value used in common practice.

18. The apparatus according to claim 17 wherein the processor is further arranged to generate a three-dimensional representation which simulates the appearance of at least the treatment area with the modified tooth set-up.

19. The apparatus according to claim 18 wherein the processor is further arranged to generate a three-dimensional representation which also simulates the appearance of the patient's face surrounding the treatment area.

\* \* \* \* \*